US012729174B2

(12) United States Patent
Zhan et al.

(10) Patent No.: US 12,729,174 B2
(45) Date of Patent: Sep. 8, 2026

(54) CONVERTING NATURAL GAS TO DIMETHYL ETHER

(71) Applicant: Saudi Arabian Oil Company, Dhahran (SA)

(72) Inventors: Guodong Zhan, Dhahran (SA); Bodong Li, Dhahran (SA); Abdulwahab S. Aljohar, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 834 days.

(21) Appl. No.: 18/081,968

(22) Filed: Dec. 15, 2022

(65) Prior Publication Data

US 2024/0199517 A1 Jun. 20, 2024

(51) Int. Cl.
*C07C 41/01* (2006.01)
*B01D 53/18* (2006.01)
(Continued)

(52) U.S. Cl.
CPC .............. *C07C 41/01* (2013.01); *B01D 53/18* (2013.01); *B01J 8/06* (2013.01); *B01J 8/24* (2013.01); *B01J 21/12* (2013.01); *B01J 23/06* (2013.01); *B01J 23/72* (2013.01); *B01J 23/755* (2013.01); *B01J 37/0219* (2013.01); *B01J 37/0221* (2013.01); *B01J 37/088* (2013.01); *C01B 3/48* (2013.01); *C07C 41/09* (2013.01); *C10L 1/1852* (2013.01); *E21B 43/16* (2013.01); *C01B 2203/0272* (2013.01); *C01B 2203/0283* (2013.01); *C01B 2203/0415* (2013.01);
(Continued)

(58) Field of Classification Search
None
See application file for complete search history.

(56) References Cited

U.S. PATENT DOCUMENTS 8,092,778 B2 1/2012 Zhu
8,147,765 B2 4/2012 Muradov
(Continued)

FOREIGN PATENT DOCUMENTS

CA 2756416 C * 6/2016 ............ C07C 41/09
CN 107376918 11/2017
(Continued)

OTHER PUBLICATIONS

Machine translation of JP2000169411A, Jun. 20, 2000, pp. 1-12 (Year: 2000).*

(Continued)

*Primary Examiner* — Medhanit W Bahta
(74) *Attorney, Agent, or Firm* — Dinsmore & Shohl LLP

(57) ABSTRACT

A system and method for converting natural gas to dimethyl ether (DME) are provided. An exemplary system includes a purified natural gas feed, a combustion chamber to combust a first portion of the natural gas to provide heat and an exhaust gas, and a separator to separate water and $CO_2$ from the exhaust gas to form a first feed, a second portion of the natural gas forms a second feed. The system also includes a bi-reforming reactor comprising a bi-reforming catalyst to react the first feed and the second feed to form hydrogen and carbon monoxide, and a dimethyl ether (DME) reactor comprising a DME catalyst to form DME from the hydrogen and carbon monoxide.

15 Claims, 4 Drawing Sheets

(51) Int. Cl.

| | |
|---|---|
| ***B01J 8/06*** | (2006.01) |
| ***B01J 8/24*** | (2006.01) |
| ***B01J 21/12*** | (2006.01) |
| ***B01J 23/06*** | (2006.01) |
| ***B01J 23/72*** | (2006.01) |
| ***B01J 23/755*** | (2006.01) |
| ***B01J 37/02*** | (2006.01) |
| ***B01J 37/08*** | (2006.01) |
| ***C01B 3/48*** | (2006.01) |
| ***C07C 41/09*** | (2006.01) |
| ***C10L 1/185*** | (2006.01) |
| ***E21B 43/16*** | (2006.01) |

(52) U.S. Cl.

CPC ................ *C01B 2203/0475* (2013.01); *C01B 2203/0495* (2013.01); *C01B 2203/061* (2013.01); *C01B 2203/063* (2013.01); *C01B 2203/1241* (2013.01); *C10L 2290/42* (2013.01)

(56) References Cited

U.S. PATENT DOCUMENTS

| | | | | |
|---|---|---|---|---|
| 9,856,197 | B2 | 1/2018 | Zubrin et al. | |
| 10,160,708 | B2 | 12/2018 | Lee et al. | |
| 2009/0208403 | A1 | 8/2009 | Hussain et al. | |
| 2012/0037363 | A1 | 2/2012 | Curole | |
| 2013/0068456 | A1* | 3/2013 | Matzakos | E21B 43/34 166/267 |
| 2013/0109888 | A1 | 5/2013 | Moon et al. | |
| 2014/0357901 | A1 | 12/2014 | Kooijman | |
| 2018/0086984 | A1 | 3/2018 | Chen et al. | |
| 2018/0155261 | A1 | 6/2018 | Raterman | |
| 2022/0089442 | A1 | 3/2022 | Zarabian et al. | |
| 2023/0347321 | A1 | 11/2023 | Alhajri et al. | |
| 2023/0382727 | A1 | 11/2023 | Dagle et al. | |
| 2024/0199424 | A1 | 6/2024 | Zhan et al. | |
| 2024/0200204 | A1 | 6/2024 | Zhan et al. | |

FOREIGN PATENT DOCUMENTS

| | | | |
|---|---|---|---|
| CN | 107376918 A | * 11/2017 | C01B 3/40 |
| CN | 111017875 | 4/2020 | |
| CN | 112705208 | 4/2021 | |
| CN | 113115580 A | 7/2021 | |
| CN | 113929054 | 1/2022 | |
| JP | 2000169411 | 6/2000 | |
| WO | WO 2013181045 | 12/2013 | |
| WO | WO 2015055349 | 4/2015 | |
| WO | WO 2021152614 | 8/2021 | |

OTHER PUBLICATIONS

Machine translation of CN 107376918A, Nov. 24, 2017, pp. 1-26 (Year: 2017).*

International Search Report and Written Opinion in International Appln. No. PCT/US2023/083531, dated Mar. 28, 2024, 12 pages.

International Search Report and Written Opinion in International Appln. No. PCT/US2023/084075, dated Apr. 17, 2024, 16 pages.

International Search Report and Written Opinion in International Appln. No. PCT/US2023/084090, dated Apr. 24, 2024, 18 pages.

Lin et al., "Vertically Aligned Carbon Nanotubes for Thermal Interface Materials: Quality Control, Alignment Improvement and Laser Flash Measurement," 2010 Proceedings 60th Electronic Components and Technology Conference (ECTC), Jun. 1-4, 2010, pp. 967-972, 6 pages.

Lin et al., "Vertically Aligned Carbon Nanotubes on Copper Substrates for Applications as Thermal Interface Materials: from Synthesis to Assembly," 2009 Electronic Components and Technology Conference, May 26-29, 2009, pp. 441-447, 7 pages.

Wang et al., "Exergy analysis of methane cracking thermally coupled with chemical looping combustion for hydrogen production," Applied Energy, Apr. 15, 2016, 168:1-12, 12 pages.

als.lbl.gov [online], "An Atomic-Level Understanding of Copper-Based Catalysts," Lawrence Berkley National Laboratory, May 2016, retrieved on Aug. 4, 2023, retrieved from URL <https://als.lbl.gov/an-atomic-level-understanding-of-copper-based-catalysts/>, 6 pages.

Chen et al., "Rational Design of Novel Catalysts with Atomic Layer Deposition for the Reduction of Carbon Dioxide," Advanced Energy Materials, 2019, 9:1900889-1900889, 26 pages.

Giglio et al., "Integration between biomass gasification and high-temperature electrolysis for synthetic methane production," Biomass and Bioenergy, 2021, 148:106017-106029, 12 pages.

Khandan et al., "Direct production of dimethyl ether from synthesis gas utilizing bifunctional catalysts," Applied Petrochemical Research, 2012, 1:21-27, 7 pages.

Lv et al., "Recent Progresses in Constructing the Highly Efficient Ni Based Catalysts With Advanced Low-Temperature Activity Toward CO2 Methanation," Frontiers in Chemistry, Apr. 2020, 8(269):1-32, 32 pages.

Otaraku et al., "Process Design of Associated Natural Gas to Dimethyl Ether Production via Direct Synthesis," International Journal of Chemical and Process Engineering Research, 2017, 5(1):1-7, 8 pages.

Rao et al., "Carbon Nanotubes and Related Nanomaterials: Critical Advances and Challenges for Synthesis toward Mainstream Commercial Applications," ACS Nano, 2018, 12:11756-11784, 29 pages.

* cited by examiner

CONVERTING NATURAL GAS TO DIMETHYL ETHER

TECHNICAL FIELD

This disclosure relates to the conversion of methane to dimethyl ether.

BACKGROUND

Natural gas and oil are often found together. However, about 40% to 60% of the world's natural gas reserves are trapped or untapped and cannot be used locally. Accordingly, about 4,500 trillion cubic feet of natural gas is stranded with little economic value. Methane is the main component of natural gas, accounting for about 87% of the volume. Upgrading low-value natural gas to an easy-to-transport liquid fuel through gas-to-liquid (GTL) conversion is a promising solution for producing this stranded resource. However, purifying GTL products into fuel and transporting the fuel by truck adds to costs, because the products formed by GTL processes are complex and natural gas reserves are often located in remote areas. Further, nearly two-thirds of conventional oil remains in reservoirs because traditional oil production methods, such as natural energy release from reservoir depressurization and water injection, cannot be produced economically. Consequently, excess methane is either burned at the site (releasing $CO_2$), or escapes into the atmosphere increasing the concentration of undesirable greenhouse gasses. Additionally, 90% or more of unconventional oils, such as shale, tight oil, and heavy oil, remain in the reservoir at the end of the oilfield's life. EOR technologies, such as heat-based EOR or gas injection EOR, offer the prospect of eventually producing another 10 to 25 percent of the remaining oil. However, some EOR techniques are not suitable for some oil fields.

SUMMARY

An embodiment disclosed in examples herein provides a method for converting natural gas to dimethyl ether. The method includes dividing a natural gas feed to form a first process feed stream and a second process feed stream, combusting the first process feed stream to provide heat for a bi-reforming reaction, and forming an exhaust stream. Water and carbon dioxide are separated from the exhaust stream, forming a stoichiometry adjustment stream. The second process feed stream and the stoichiometry adjustment stream are fed to a pre-reforming reaction, forming a pre-reformed effluent stream. The pre-reformed effluent stream is fed to a bi-reforming reaction, forming a metgas effluent stream. The metgas effluent stream is fed to a DME reaction, forming a DME effluent stream. The DME effluent stream is passed through a water absorber to form an aqueous DME solution.

Another embodiment described in examples herein provides a system for converting natural gas to dimethyl ether (DME). The system includes a purified natural gas feed, a combustion chamber to combust a first portion of the natural gas to provide heat and an exhaust gas, and a separator to separate water and $CO_2$ from the exhaust gas to form a first feed, a second portion of the natural gas forms a second feed. The system also includes a bi-reforming reactor comprising a bi-reforming catalyst to react the first feed and the second feed to form hydrogen and carbon monoxide, and a dimethyl ether (DME) reactor comprising a DME catalyst to form DME from the hydrogen and carbon monoxide.

DETAILED DESCRIPTION

Embodiments described herein provide a method and system for converting natural gas (mainly methane) into dimethyl ether (DME). The DME can be used directly as a propellant for enhanced oil recovery (EOR). The use of dimethyl ether has proven to be technically effective, safe to operate, and an environmentally sound procedure. The conversion process can be implemented at the production site, further lowering cost by decreasing transportation costs.

A modular reactor system is used for the conversion, including a bi-reforming reactor that is designed for process enhancement, a catalyst designed for methane bi-reforming and a bifunctional catalyst design for dimethyl ether synthesis. The bifunctional catalyst is used to convert syngas, or metgas, to methanol, and dehydrate the methanol dehydrated to form the DME. The catalysts are prepared by atomic layer deposition (ALD) and additive manufacturing. The DME can be isolated from the mixture of gas products using a water absorption process, forming an aqueous solution of DME. The aqueous solution of DME may be directly used as a propellant for enhanced oil recovery. In some embodiments, the aqueous solution of DME or the DME formed in the reactor can be processed and used as a fuel, such as a replacement for diesel.

The technology described herein could be applied to other reservoirs where stranded natural gas can be used to make dimethyl ether. As the techniques capture and process natural gas that would otherwise be flared, they enhance the economics of the production. Additionally, the use of the DME is a non-thermal EOR technique that does not thaw permafrost like some other EOR methods.

Figure 1:
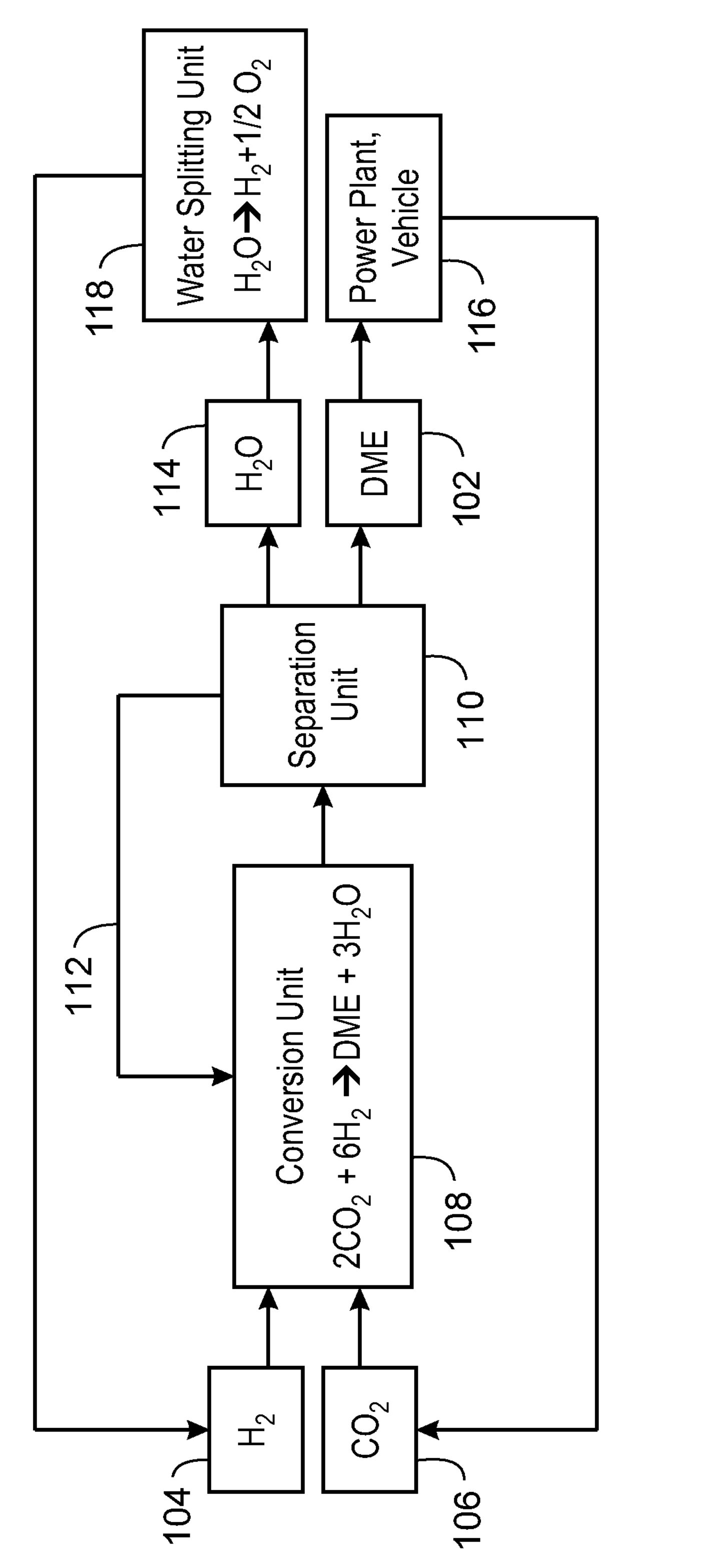
FIG. 1 is a simplified block diagram of a system for forming DME from natural gas.

FIG. 1 is a schematic diagram 100 of the formation of DME 102 from H2 104 and CO2 106. The H2 104 and CO2 106 are fed to a conversion unit 108 that used a bi-functional catalyst, for example, as described herein, to convert the H2 104 and CO2 106 to DME and water. In some embodiments, as described herein, the H2 104 and CO2 106 are generated in a bi-reforming reaction from natural gas and water. The effluent from the conversion unit 108 is then fed to a separation unit 110.

In the separation unit 110, excess gases 112 are separated from the DME 102 and the H2O 114. The excess gases 112, including H2 and CO2, are recycled to the conversion unit 108. The water 114 can be used as a source of water, for example, in dry or desert locations. In some embodiments, the water 114 is used as a feed to a water-splitting unit 118 to generate a portion of the H2 104 for the reaction. The water-splitting unit 118 can be powered by renewable resources, such as solar or wind power. The water 114 may also be used in the bi-reforming reaction that generates H2 104 and CO2 106.

The DME 102 can be further purified to form a product, such as a fuel that can be provided to a power plant and vehicles 116. Burning the DME 102 forms carbon dioxide, which can be purified and recycled as a portion of the CO2 106 used for the reaction. In some embodiments, as discussed below, the DME 102 is dissolved in water for purification and used as an enhanced oil recovery (EOR) propellant.

Figure 2:
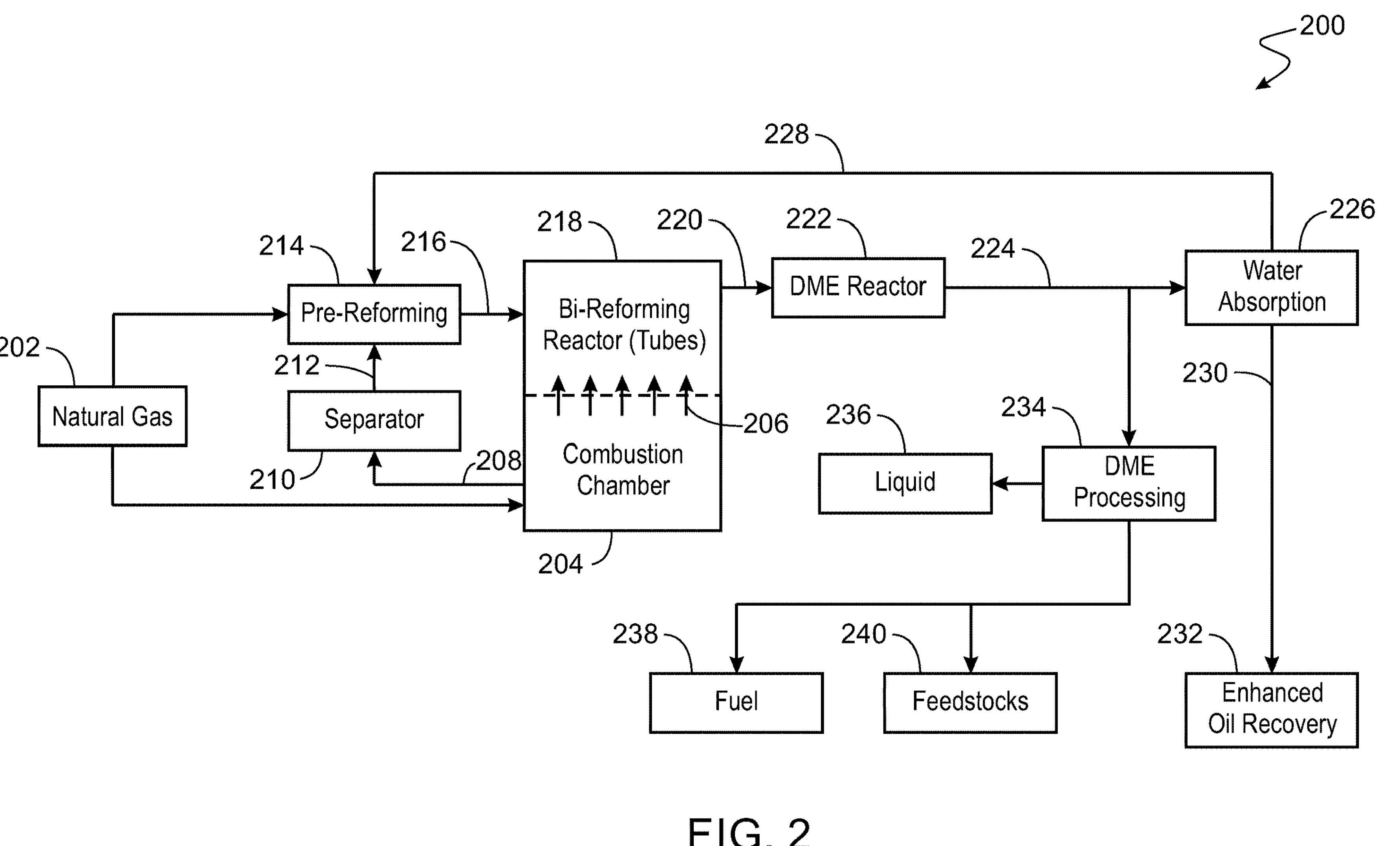
FIG. 2 is a simplified block diagram of a system 200 for forming DME from natural gas.

FIG. 2 is a simplified block diagram of a system 200 for forming DME from natural gas. The system 200 is fed natural gas 202, for example, stranded natural gas from an oil or gas field. The natural gas 202 can be purified before use, for example, by the removal of acid gases such as hydrogen sulfide or carbon dioxide in an adsorption unit. In some embodiments, the adsorption unit (not shown) is a column of molecular sieves, such as zeolites. Generally, two columns are used, with the process alternating between each column, wherein one column is adsorbing impurities while the other column is being regenerated. In other embodiments, the adsorption unit is a countercurrent column using a lean amine stream as an absorbent. A regeneration column is then used to strip the acid gases from a rich amine stream formed during the process, regenerating the lean amine stream.

The natural gas 202 is divided into two process feed streams. A first process feed stream is fed to a combustion chamber 204 which is used to generate heat 206 for the process. Oxygen is fed to the combustion chamber 204 with the natural gas 202 combusting the natural gas, providing an exhaust gas 208 that includes water and carbon dioxide. The use of the natural gas to provide the heat used for the process lowers the energy demands and improves the economics.

The exhaust gas 208 enters a separator 210 to form a stoichiometry adjustment stream 212 that includes the water and carbon dioxide. The separator 210 can include a condenser, or a membrane separator, among others. The amount of water and carbon dioxide in the stoichiometry adjustment stream 212 are controlled to provide the correct stoichiometry to improve the yields of downstream processes.

A second process feed stream from the natural gas 202 is fed to a pre-reforming reactor 214 along with the stoichiometry adjustment stream 212. In various embodiments, the pre-reforming reactor 214 is a tube reactor, a fluidized bed reactor, or a countercurrent reactor, among others. The pre-reforming reactor 214 includes a catalyst, for example, nickel deposited on an alumina surface, as described below. The pre-reforming reactor 214 is operated at temperatures of between about 400° C. and about 500° C. While methane is stable at these conditions, higher hydrocarbons ($C_{2+}$) will be converted to hydrogen, carbon oxides, and methane.

The effluent 216 from the pre-reforming reactor 214 is fed to a bi-reforming reactor 218, which is heated by the combustion chamber 204. In some embodiments, the bi-reforming reactor 218 is a tubular reactor with a catalyst disposed on an interior surface of the tubes. The exterior surface of the tubes is within the combustion chamber 204. In other embodiments, the bi-reforming reactor 218 is a fluidized bed reactor in which the effluent 216 from the pre-reforming reactor 214 fluidizes catalyst particles. In this embodiment, the combustion chamber 204 surrounds vertical tubes that hold the fluidized catalyst particles.

The bi-reforming reactor 218 generates metgas 220, which is a mixture of hydrogen and carbon monoxide. In the bi-reforming reaction, a dry reforming reaction generates hydrogen and carbon monoxide from methane and carbon dioxide, while a steam reforming process generates hydrogen and carbon monoxide from the reaction of methane and water. The reactions in the bi-reforming of methane are:

$$CH_4+CO_2 \rightleftharpoons 2H_2+2CO \quad \text{(dry reforming):}$$

$$CH_4+H_2O \rightleftharpoons 3H_2+CO \quad \text{(steam reforming):}$$

with a final stoichiometry of $$3CH_4+2H_2O+CO_2 \rightleftharpoons 8H_2+4CO \quad \text{(overall stoichiometry).}$$

The presence of both the dry reforming and the steam reforming reactions enables a final molar ratio of hydrogen to carbon monoxide in the metgas 220 of 2:1. To further control this, the composition of the stoichiometry adjustment stream 212 from the separator 210 to the pre-reforming reactor 214 can be adjusted. The ratio between the two process feed streams from the natural gas 202 is also adjusted, wherein the first process feed stream about one quarter of the natural gas 202 is combusted in the combustion chamber 204 and the other three quarters of the natural gas 202 is fed to the pre-reforming reactor 214. The 2:1 ratio between the hydrogen and carbon monoxide in the metgas 220 optimizes the production of methanol, and, thus, DME from the metgas 220.

The catalyst used for the bi-reforming reaction includes an alumina surface that is generated by atomic layer deposition of alumina over a substrate. A catalytically active metal, such as nickel, is deposited on the alumina. In various embodiments, the catalytically active metal can include nickel, cobalt, or platinum, among others, such as rhodium, iridium, palladium, or ruthenium. A combination of metals may be used to enhance the reaction. The formation of the catalyst is described further with respect to FIGS. 3A and 3B. The bi-reforming reactor 218 operates at 700-850° C. and low pressure, such as about 5 psig to about 50 psig, forming the metgas 220.

The metgas 220 from the bi-reforming reactor 218 is fed to a DME reactor 222. The DME reactor 222 can also be a tubular reactor with catalyst coated on the interior surface of the tubes. In some embodiments, the DME reactor 222 is a fluidized bed reactor, in which catalyst particles are fluidized by the flow of the metgas 220 from the bi-reforming reactor 218.

The DME reactor 222 includes a bifunctional catalyst that generates methanol from the hydrogen and carbon monoxide of the metgas 220, then dehydrates the methanol to generate the DME. In some embodiments, the bifunctional catalyst includes an alumina surface generated by atomic layer deposition of alumina over a substrate. A catalytically active metal is then deposited on the alumina. In some embodiments, a Cu-based catalyst, such as $CuO/ZnO/Al_2O_3$, is used for the methanol synthesis:

$$CO+2H_2 \rightleftharpoons CH_3OH.$$

This reaction yield is limited by the equilibrium with the reverse reaction, reforming the CO and $H_2$. An acid catalyst, such as a commercially available acidic zeolite, H-ZSM-5, is used for the dehydration of the methanol:

$$CH_3OH \rightleftharpoons CH_3OCH_3+H_2O.$$

The dehydration reaction removes the methanol formed in the first reaction, shifting the equilibrium of the methanol synthesis, providing a high yield for the overall reaction:

$$2CO+4H_2 \rightleftharpoons CH_3OCH_3+H_2O$$

The water-gas shift reaction (WGS) is a side reaction:

$$CH_3OH \rightleftharpoons CH_3OCH_3+H_2O$$

Thus, the water formed as a by-product can severely affect the overall yield of the reaction. However, the water may be removed as a vapor, lowering the effect on the reaction.

The effluent 224 from the DME reactor 222 is fed to a water absorption system 226 to remove the DME from the effluent 224. In some embodiments of the water absorption system 226, the effluent 224 is cooled in a heat exchanger and then bubbled through a water column in an absorber tower. In the absorber tower, water is used to absorb DME, and other oxygenates, including excess methanol and a portion of the $CO_2$. The vapor stream 228 from the absorber tower, including $H_2$, CO, and the remaining portion of the $CO_2$, is recycled for DME synthesis. The liquid stream 230 including $H_2O$, DME, MeOH, and $CO_2$, may be used as a concentrated DME solution for EOR 232. As compared to the complicated separation for traditional DME production, the absorber tower could directly produce the liquid stream 230, significantly decreasing capital, and operating costs.

In some embodiments, the DME may be used or sold for other purposes. In these embodiments, a DME processing system 234 may be used to process the effluent 224 from the DME reactor 222, for example, by passing the effluent through a chiller to condense a liquid stream 236, including $H_2O$ and MeOH, from the gases, such as the CO, $CO_2$, and DME. The CO and $CO_2$ can then be removed by cryogenic separation, adsorption, or other techniques. The resulting DME can then be used as a fuel 238 or a feedstock 240.

Figures 3A, 3B:
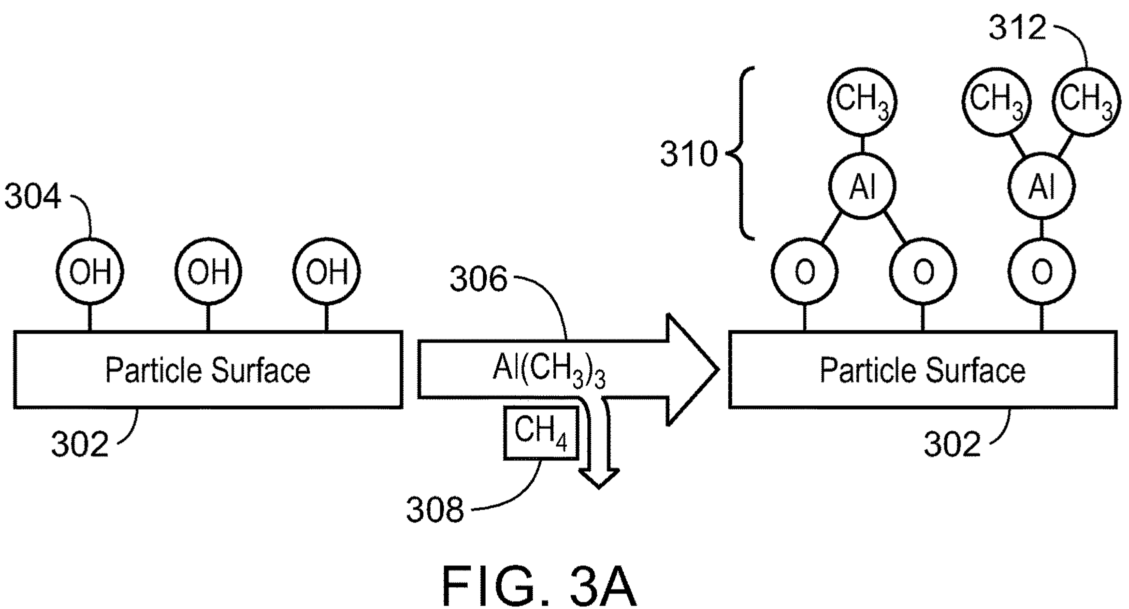
FIGS. 3A and 3B are drawings of the surface of the catalyst showing the deposition of atomic layers of alumina on a surface to form a catalyst.

FIGS. 3A and 3B are drawings of the surface of the catalyst showing the deposition of atomic layers of alumina to form a catalyst. This process is used to generate both the catalyst for the bi-reforming reaction and the bifunctional catalyst used for producing the DME. As shown in FIG. 3A, a catalyst support 302 has hydroxyl groups 304. In various embodiments, the catalyst support 302 is formed from silica, alumina, or another metal oxide. The catalyst support 302 may be a particulate or a solid surface of an interior of a tube. The particulate can be chosen to lower catalyst costs, such as using a silica sand.

The catalyst support 302 is treated by contact with an excess of trimethyl aluminum (TMA), $Al(CH_3)_3$, 306. The TME 306 reacts with the hydroxyl groups 304, releasing methane 308, and forming a layer 310 over the catalyst support 302 that includes methyl groups 312 as the outer surface. The reaction is limited by the number of hydroxyl groups 304, first slowing, and then stopping as the hydroxyl groups 304 are exhausted. For example, the surface reaction may include 90% of the hydroxyl groups 304, 95%, 99%, or higher, depending on contact time.

FIG. 3B shows the second step of the reaction. After the TMA treatment, the catalyst support 302 is further treated by contact with an excess of water 314. The water 314 reacts with the methyl groups 312, releasing further methane 308, and forming a layer of alumina 316 over the catalyst support 302. As for the reaction in FIG. 3A, the reaction in FIG. 3B is limited by the number of methyl groups 312, first slowing, and then stopping as the methyl groups 312 are exhausted. As this is a very active reaction, most, or all, of the methyl groups 312 will be displaced. The surface reaction may include 95% of the methyl groups 312, 99%, or higher, depending on contact time. The reactions in FIGS. 3A and 3B may be iterated to form additional layers over the catalyst support 302, such as one layer of alumina 316, two layers of alumina 316, three layers of alumina 316, or more. For a catalyst support 302 in a particulate form, the iteration of the procedure described by FIGS. 3A and 3B produces a coated particle. If the catalyst support 302 is a particulate, the reactions shown in FIGS. 3A and 3B can be performed in a fluidized bed reactor or a rotary reactor, among others.

Once the desired number of layers have been deposited, other catalysts may be deposited over the alumina surface of the coated particle, such as copper oxide/zinc oxide, nickel, platinum, palladium, or ruthenium, or other metals as described herein. In some embodiments, the additional metals are deposited by mixing the coated particles with a solution of the target metal as a salt, then drying the solution, and calcining to form the final catalyst.

For example, to form a catalyst with nickel domains, the catalyst support 302 can be treated by immersion in a solution of a nickel salt, such as solution of nickel nitrate ($Ni(II)(NO_3)_2$). The catalyst support 302 is then removed from the solution, or the solution is drained from the reactor. The catalyst support 302 is then dried, for example, being heated to a temperature of between 50° C. and 100° C., or to a temperature of less than about 100° C. After drying, the catalyst support 302 may be calcined at a higher temperature, such as between 500° C. and 700° C. A reducing atmosphere, such as a mixture of nitrogen and hydrogen, is used to reduce the nickel to the metallic form, producing nickel metal domains over the surface. The size of the domains may be controlled by the amount of the nickel solution used, and the number of repetitions of the treatment with the solution. In some embodiments, a continuous film is formed by multiple cycles of addition of the solution, each followed by treatment in a reducing atmosphere. Similar processes may be used to add domains of other metals, such as cobalt, platinum, palladium, ruthenium, and the like. If the catalyst support 302 is a particulate, the treatment with the solution may be performed with the particulates in a fluidized state, wherein the metal salt solution is entrained with the gas use for the fluidization.

Similarly, to form a CuO/ZnO/alumina catalyst, the catalyst support 302 is treated with a solution containing a copper salt and a zinc salt, such as a solution of copper sulfate and zinc sulfate, for example, using the same procedures as described for the nickel salts. After treatment with the copper sulfate and zinc sulfate solution, the catalyst support 302 is dried at a low temperature, such as below about 100° C., or between 50° C. and 100° C. This can be followed by calcining at a higher temperature, such as between 500° C. and 700° C. in an inert atmosphere, resulting in the formation of the CuO/ZnO domains over the alumina surface of the catalyst support 302. In this example, a reducing atmosphere is not used as the copper and zinc ions are used in an oxidized state.

Figure 4:
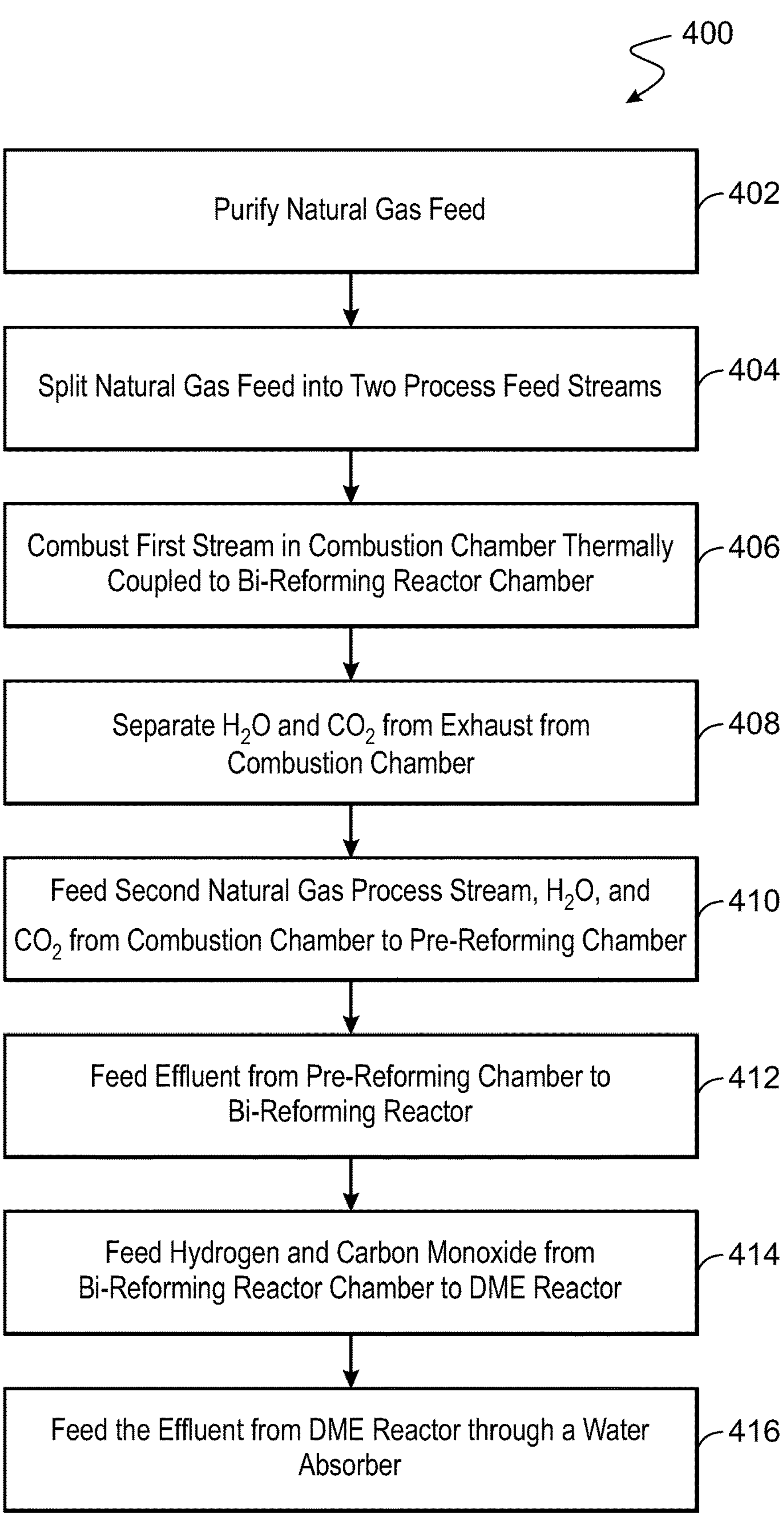
FIG. 4 is a block diagram of a method for forming DME from natural gas.

FIG. 4 is a block diagram of a method 400 for forming DME from natural gas. The method 400 begins at block 402 with the purification of a natural gas feed. As described herein, the natural gas may include contaminants such as hydrogen sulfide. In various embodiments, the hydrogen sulfide is removed using an amine absorption system, a zeolite adsorption column, and the like. Other contaminants can include mercury, arsenic, or chlorine, which may be removed by similar techniques.

At block 404, the natural gas feed is split into two process feed streams, a first process feed stream and a second process feed stream. The ratio between the first process feed stream and the second process feed stream can be adjusted to control the stoichiometry of downstream reactions.

At block 406, the first process feed stream is combusted in a combustion chamber providing energy for the process and an exhaust stream. As described herein, oxygen can be added to the combustion chamber for the combustion. However, air may be used if oxygen purification systems are not available. In this case, though, the nitrogen from the air will dilute the combustion products. Further, the nitrogen will form NOxs, depending on the temperature of the combustion. The NOxs may be poisonous to the catalysts.

At block 408, the exhaust stream is separated to form a stoichiometry adjustment stream including water and carbon dioxide. The composition of the stoichiometry adjustment stream can be determined by the units used to form the stoichiometry adjustment stream, for example, the $CO_2$ may be purified by a membrane separator, while a portion of the water can be removed by condensation. The amount of water removed can be controlled by adjusting the flow through the condenser.

At block 410, the second process feed stream is fed, along with the water and carbon dioxide to a pre-reforming reactor. In the pre-reforming reactor, higher hydrocarbons (C2+) will be converted to hydrogen, carbon oxides, and methane.

At block 412, the effluent from the pre-reforming reactor is fed to a bi-reforming reactor. As discussed herein, the methane, hydrogen, and carbon oxides from the pre-reforming reactor is converted to metgas, which is a syngas with a 2:1 ratio of hydrogen to carbon monoxide.

At block 414, the effluent from the bi-reforming reactor is fed to a DME reactor. As discussed herein, in the DME reactor, the hydrogen and carbon monoxide in the effluent from the bi-reforming reactor are first converted to methanol, which is then dehydrated to form the DME.

At block 416, the effluent from the DME reactor is fed to a water absorber, which absorbs the DME and methanol in the effluent gases. The aqueous solution may then be used directly as an enhanced oil recovery propellant, for example, by being injected into a reservoir. The direct use of the aqueous solution eliminates the need for further purification steps, lowering the overall costs.

However, in some embodiments, the DME is further processed for use in other applications. For example, in some embodiments, the aqueous solution is shipped to a refinery or chemical plant for further purification and use. In other embodiments, the effluent from the DME reactor is directly processed for other applications, such as fuel. In these embodiments, water and methanol from the reactor effluent may be removed by a condenser, followed by condensing the DME in a chiller.

EMBODIMENTS

An embodiment disclosed in examples herein provides a method for converting natural gas to dimethyl ether. The method includes dividing a natural gas feed to form a first process feed stream and a second process feed stream, combusting the first process feed stream to provide heat for a bi-reforming reaction, and forming an exhaust stream. Water and carbon dioxide are separated from the exhaust stream, forming a stoichiometry adjustment stream. The second process feed stream and the stoichiometry adjustment stream are fed to a pre-reforming reaction, forming a pre-reformed effluent stream. The pre-reformed effluent stream is fed to a bi-reforming reaction, forming a metgas effluent stream. The metgas effluent stream is fed to a DME reaction, forming a DME effluent stream. The DME effluent stream is passed through a water absorber to form an aqueous DME solution.

In an aspect, the method includes removing hydrogen sulfide from the natural gas prior to forming the first process feed stream and the second process feed stream.

In an aspect, the method includes adjusting an amount of water and carbon dioxide in the stoichiometry adjustment stream based, at least in part, on the amount of methane in the second process feed stream.

In an aspect, the method includes adjusting a ratio between the first process feed stream and the second process feed stream based, at least in part, on the bi-reforming reaction.

In an aspect, the method includes adjusting a ratio between the first process feed stream and the second process feed stream to achieve a hydrogen to carbon monoxide ratio in the metgas effluent stream of 2:1.

In an aspect, the method includes injecting the aqueous DME solution into a reservoir for enhanced oil recovery.

In an aspect, the method includes treating a catalyst support including hydroxyl groups with an excess of trimethyl alumina to form a layer over the catalyst support including methyl groups, and treating the catalyst support including the methyl groups with water to form a catalyst support including an alumina layer. In an aspect, the method includes repeating the treatment with the trimethyl alumina and the water to form multiple alumina layers over the catalyst support.

In an aspect, the catalyst support includes the surface of a particle.

In an aspect, the particle includes silica sand.

In an aspect, the method includes forming a catalyst from the catalyst support. This is performed by treating the catalyst support with a metal salt, drying the catalyst support at a first temperature, wherein the first temperature is between about 50° C. and about 100° C., and calcining the catalyst support at a second temperature, wherein the second temperature is between about 500° C. and 700° C. in an aspect, the calcining of the catalyst support is performed in a reducing atmosphere. In an aspect, the calcining of the catalyst support is performed in an inert atmosphere. In an aspect, the metal salt comprises nickel. In an aspect, the metal salt comprises copper. In an aspect, the metal salt comprises zinc.

Another embodiment described in examples herein provides a system for converting natural gas to dimethyl ether (DME). The system includes a purified natural gas feed, a combustion chamber to combust a first portion of the natural gas to provide heat and an exhaust gas, and a separator to separate water and $CO_2$ from the exhaust gas to form a first feed, a second portion of the natural gas forms a second feed. The system also includes a bi-reforming reactor comprising a bi-reforming catalyst to react the first feed and the second feed to form hydrogen and carbon monoxide, and a dimethyl ether (DME) reactor comprising a DME catalyst to form DME from the hydrogen and carbon monoxide.

In an aspect, the system includes a water absorber to absorb DME from a reactor effluent of the DME reactor.

In an aspect, the system includes a DME processor to prepare the DME for applications. In an aspect, the system includes a product fuel stream comprising DME. In an aspect, the system includes an enhanced oil recovery product stream comprising DME.

Other implementations are also within the scope of the following claims.

What is claimed is:

1. A method for converting natural gas to dimethyl ether, comprising:

dividing a natural gas feed to form a first process feed stream and a second process feed stream;

combusting the first process feed stream to provide heat for a bi-reforming reaction, and forming an exhaust stream;

separating water and carbon dioxide from the exhaust stream, forming a stoichiometry adjustment stream;

feeding the second process feed stream and the stoichiometry adjustment stream to a pre-reforming reaction, forming a pre-reformed effluent stream;

feeding the pre-reformed effluent stream to a bi-reforming reaction, forming a metgas effluent stream;

feeding the metgas effluent stream to a DME reaction, forming a DME effluent stream; and passing the DME effluent stream through a water absorber to form an aqueous DME solution, wherein the bi-reforming reaction and the DME reaction are conducted in the presence of a catalyst supported on a catalyst support comprising an alumina layer formed by:

treating a catalyst support comprising hydroxyl groups with an excess of trimethyl alumina to form a layer over the catalyst support comprising methyl groups; and treating the catalyst support comprising the methyl groups with water to form the catalyst support comprising an alumina layer.

2. The method of claim 1, comprising removing hydrogen sulfide from the natural gas prior to forming the first process feed stream and the second process feed stream.

3. The method of claim 1, comprising adjusting an amount of water and carbon dioxide in the stoichiometry adjustment stream based, at least in part, on the amount of methane in the second process feed stream.

4. The method of claim 1, comprising adjusting a ratio between the first process feed stream and the second process feed stream based, at least in part, on the bi-reforming reaction.

5. The method of claim 1, comprising adjusting a ratio between the first process feed stream and the second process feed stream to achieve a hydrogen to carbon monoxide ratio in the metgas effluent stream of 2:1.

6. The method of claim 1, comprising injecting the aqueous DME solution into a reservoir for enhanced oil recovery.

7. The method of claim 1, comprising repeating the treatment with the trimethyl alumina and the water to form multiple alumina layers over the catalyst support.

8. The method of claim 1, wherein the catalyst support comprises the surface of a particle.

9. The method of claim 8, wherein the particle comprises silica sand.

10. The method of claim 1, comprising forming the catalyst from the catalyst support, comprising:

treating the catalyst support with a metal salt;

drying the catalyst support at a first temperature, wherein the first temperature is between about 50° C. and about 100° C.; and calcining the catalyst support at a second temperature, wherein the second temperature is between about 500° C. and 700° C.

11. The method of claim 10, wherein the calcining of the catalyst support is performed in a reducing atmosphere.

12. The method of claim 10, wherein the calcining of the catalyst support is performed in an inert atmosphere.

13. The method of claim 10, wherein the metal salt comprises nickel.

14. The method of claim 10, wherein the metal salt comprises copper.

15. The method of claim 10, wherein the metal salt comprises zinc.

* * * * *